US010981014B2

(12) United States Patent
Taylor et al.

(10) Patent No.: US 10,981,014 B2
(45) Date of Patent: Apr. 20, 2021

(54) DUAL SEQUENTIAL DEFIBRILLATION SYSTEMS AND METHODS

(71) Applicant: The UAB Research Foundation, Birmingham, AL (US)

(72) Inventors: Tyson G. Taylor, Bothell, WA (US); Fred W. Chapman, New Castle, WA (US); Gregory Walcott, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 216 days.

(21) Appl. No.: 15/944,703

(22) Filed: Apr. 3, 2018

(65) Prior Publication Data

US 2018/0280709 A1    Oct. 4, 2018

Related U.S. Application Data

(60) Provisional application No. 62/480,647, filed on Apr. 3, 2017.

(51) Int. Cl.
*A61N 1/39* (2006.01)
*G16H 40/60* (2018.01)
*G16H 20/30* (2018.01)
*G16H 40/67* (2018.01)
*G16H 40/63* (2018.01)

(52) U.S. Cl.
CPC ......... *A61N 1/3987* (2013.01); *A61N 1/3904* (2017.08); *A61N 1/3925* (2013.01); *A61N 1/3993* (2013.01); *G16H 20/30* (2018.01); *G16H 40/60* (2018.01); *G16H 40/63* (2018.01); *G16H 40/67* (2018.01)

(58) Field of Classification Search
CPC .. A61N 1/3987; A61N 1/3925; A61N 1/3904; A61N 1/3993; G16H 20/30; G16H 40/67; G16H 40/63; G16H 40/60
See application file for complete search history.

(56) References Cited

U.S. PATENT DOCUMENTS

| 4,708,145 A | * | 11/1987 | Tacker, Jr. | A61N 1/3918 |
| | | | | 607/5 |
| 8,498,181 B1 | * | 7/2013 | Bath | G06F 3/04886 |
| | | | | 368/243 |
| 9,067,080 B2 | * | 6/2015 | Einy | A61N 1/39 |

OTHER PUBLICATIONS

Abstract for the 2018 NAWMSP Scientific Assembly, Prehospital Emergency Care, 22:1, 101-150, https://doi.org/10.1080/10903127.2017.1377791.

(Continued)

*Primary Examiner* — Mark Bockelman
(74) *Attorney, Agent, or Firm* — Lee & Hayes, P.C.

(57) ABSTRACT

Dual sequential defibrillation (DSD) systems and methods include the use of a timing device. The timing device can assist a user with DSD administration by providing notifications spaced apart by the inter-shock timing. The user can use these notifications to trigger the administration of defibrillation in a sequential manner. The timing device can also be coupled to two defibrillation devices and can output a signal to each of the defibrillation devices to cause the defibrillation device to administer a defibrillation. The output of the signals by the timing device can be spaced apart by the inter-shock timing. Additionally, the signals can be QRS-like in nature to cause the defibrillation devices to administer a defibrillation when in a sync mode.

19 Claims, 6 Drawing Sheets

(56) References Cited

OTHER PUBLICATIONS

Johnson et al., "Effect of pulse separation between two sequential biphasic shocks given over differnet lea doncfiurations on ventricular defibrillation efficacy", Circulation, 85(6), 2267-2274, https://doi.org/10.1161/01.CIR.85.6.2267, 1992.

Jones et al., "Improved internal defibrillation with twin pulse sequential energy delivery to different lead orientations in pigs", The American Journal of Cardiology, 55(6), 821-825, https://www.doi.org/10.1016/0002-9149(85)90163-8, Mar. 1, 1985.

Cooper et al., "The effect of phase separation on biphasic waveform defibrillation", Pacing and Clinical Electrophysiology, 16(3 pt 1), 471-482, https://www.ncbi.nlm.nih.gov/pubmed/7681199, Mar. 6, 1991.

Sweeney et al., "Double-pulse defibrillation using pulse spearation based on the fibrillation cycle length", Journal of Cardiovascular Electrophysiology, 5(9), 761-70, Retrieved from http://www.ncbi.nlm.nih.gov/pubmed/7827715, 1994.

McDaniel et al., "Double pulse transthoracic defibrillation in the calf using percent fibrillation cycle length as spacing determinate", Pacing and Clinical Electrophysiology: PACE, 22(10), 1440-7, Retrieved from http://www.ncbi.nlm.nig.gov/pubmed/10588145, 1999.

KenKnight et al., "Marked reduction of ventricular defibrillation threshold by application of an auxiliary shock to a catheter electrode in the left posterior coronary vein of dogs", Journal of Cardiovascular Electrophysiology, 11(8), 900-6, Retrived from http://www.ncbi.nlm.nih.gov/pubmed/10969753, 2000.

Walker et al., "Critically timed auxiliary shock to weak field area lowers defibrillation threshold", Journal of Cardiovascular Eelctrophysiology, 12(5), 556-62, Retrieved from http://www.ncbi.nlm.nih.gov/pubmed/11386517, 2001.

Jones et al., "Internal ventricular defibrillation with sequential pulse countershock in pigs: comparison with single pulses and effects of pulse separation", Pacing and Clinical Electrophysiology: PACE, 10(3 Pt 1), 497-502, Retrieved from http://www.ncbi.nlm.nih.gov/pubmed/2439998, 1987.

Merchant et al., "Do We Have a Common Mechanism for Measuring Time in the Hundreds of Millisecond Range? Evidence From Multiple-Interval Timing Tasks", Journal of Neurophysiology, 99(2), 939-949, https://doi.org/10.1152/in.012252007, 2008.

Zarco et al., "Subsecond Timing in Primates: Comparison of Interval Production between Human Subjects and Rhesus Monkeys", Journal of Neurophysiology, 102(6), 3191.3202, https://doi.org/10.1152/jn.00066.2009, 2009.

* cited by examiner

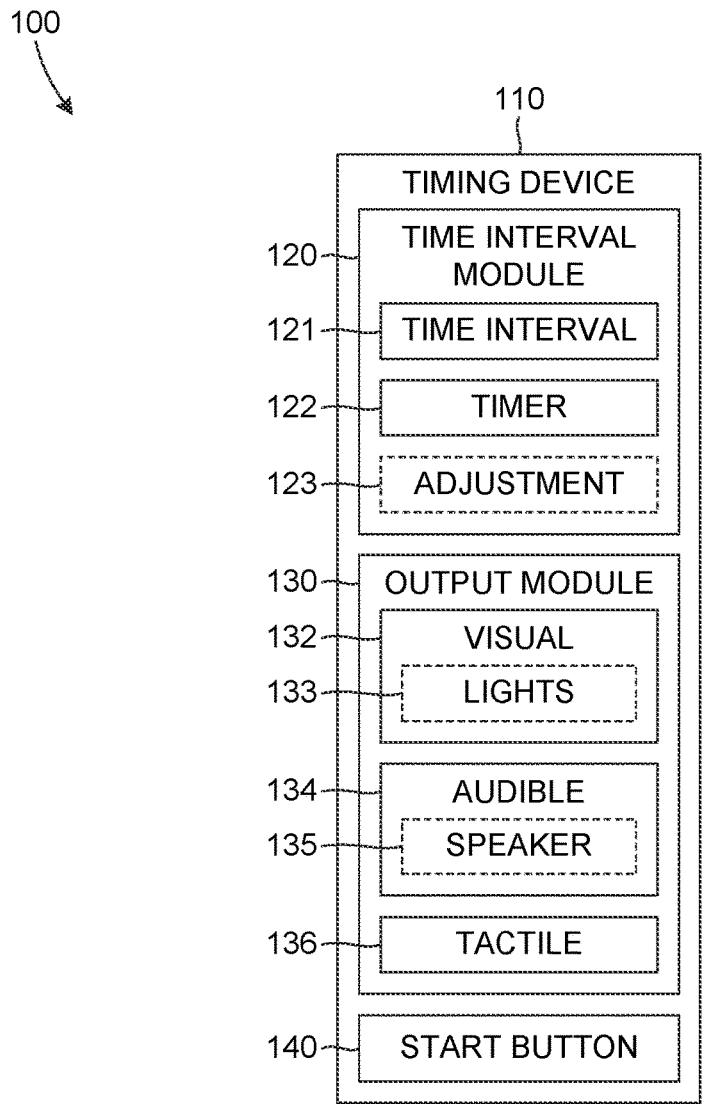
FIG. 1

DUAL SEQUENTIAL DEFIBRILLATION SYSTEMS AND METHODS

CROSS-REFERENCE TO RELATED APPLICATIONS

This patent application claims the benefit of and priority to U.S. Provisional Patent Application Ser. No. 62/480,647 filed on Apr. 3, 2017 entitled "Devices and Methods to Perform Double Sequential External Defibrillation with Controlled Inter-shock Timing," the contents of which are hereby incorporated by reference in their entirety.

BACKGROUND

Dual sequential defibrillation (DSD), is a treatment protocol that is growing in use and popularity to treat patients suffering from cardiac arrest. For a patient in ventricular fibrillation, and especially for a patient suffering from recurrent and uncontrolled ventricular fibrillation, the use of DSD or simultaneous defibrillation can be an effective treatment in restoring the patient's normal heart rhythm. DSD is considered by rescuers as a desperate last ditch effort to save the life of a cardiac arrest victim. Administration of DSD can be haphazard, poorly timed, and uncoordinated. DSD involves sequential defibrillations administered using two separate defibrillators, such as an automated external defibrillator (AED) and/or a standard defibrillator or monitor/defibrillator. Human rescuers have been observed to manually time the two (or more) defibrillation shocks to be delivered to the patient spaced apart by an inter-shock timing interval. Depending on the type of arrhythmia experienced by the patient, the timing of the shocks is different and the precision with which the shocks must be delivered for effective treatment is of great importance.

Relying on human ability and/or judgment to administer shocks from two separate defibrillators in a coordinated manner is an imperfect system that often results in ineffective therapy outcomes due to improper inter-shock timing. Improper timing of the sequential shock delivery can also lengthen the time a patient experiences the cardiac event and treatment or can cause fatal additional arrhythmias to the patient's heart.

There exists a need for systems and/or methods that improve the accuracy of the inter-shock timing in a dual sequential defibrillation administration.

BRIEF DESCRIPTION OF THE DRAWINGS

FIG. 1 illustrates an example dual sequential defibrillation system.

DETAILED DESCRIPTION

Figure 2:
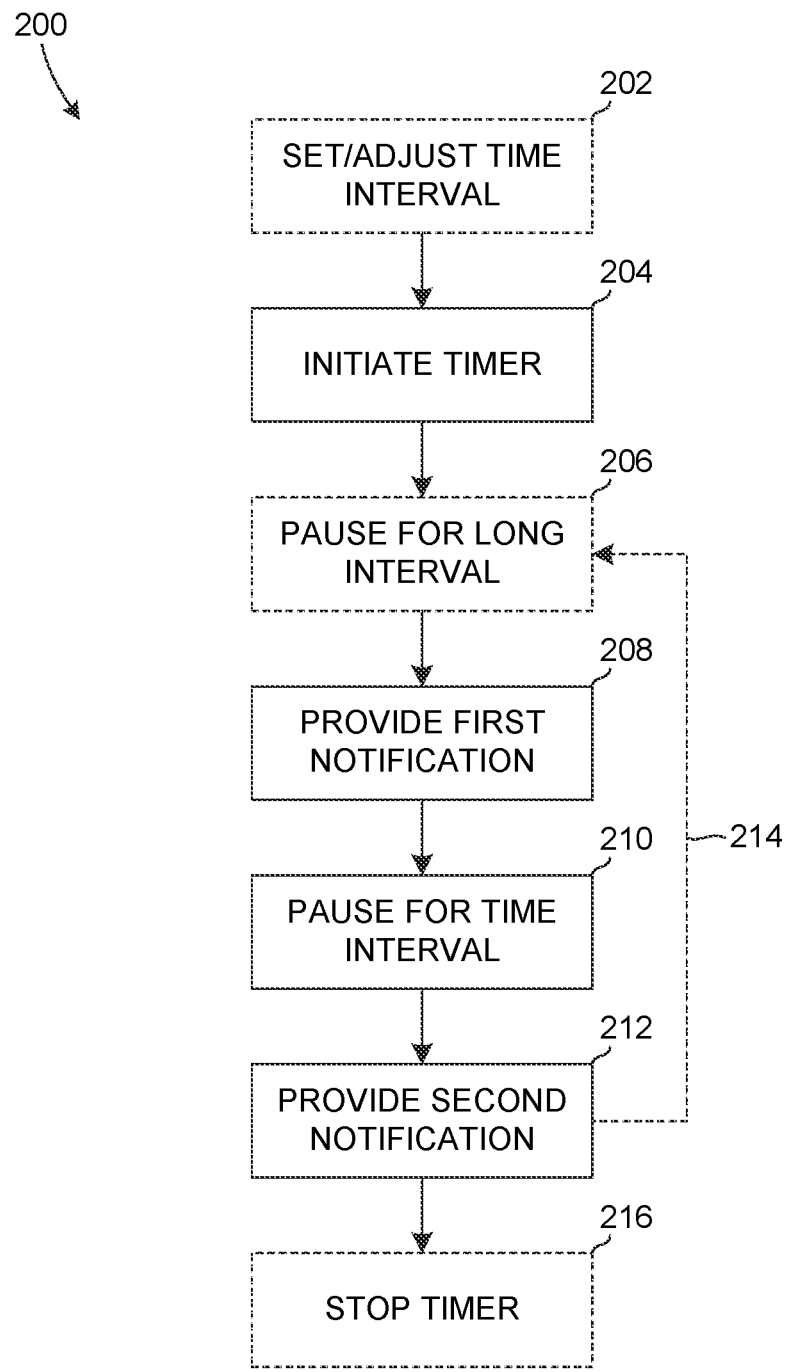
FIG. 2 illustrates an example method of timing a dual sequential defibrillation.

Systems and methods of dual sequential defibrillation (DSD) are discussed herein. The systems and methods control the inter-shock timing of DSD administration. That is, control of the spacing/duration between administration of a first electrotherapy and administration of a second electrotherapy. A timing device can provide notifications to assist a user with manually delivering sequential defibrillations spaced apart by the inter-shock timing interval. In another embodiment, a timing device can output signals directly to the defibrillation devices to cause the defibrillation devices to administer a defibrillation from each, the administration of the defibrillations spaced apart by the inter-shock timing interval. The inter-shock timing interval can be set, and/or determined, such that the defibrillations are administered substantially simultaneously, such as a zero or null inter-shock timing interval, or sequentially, such as a first defibrillation followed by a second defibrillation separated from the first by the inter-shock timing interval. Additionally, the sequentially administered defibrillations can be administered such that the later administered defibrillation at least partially overlaps with the administration of the earlier defibrillation. The partially overlapping defibrillations can be separated by an inter-shock timing interval that is less than the duration of the initial shock. Further, the inter-shock timing interval can be dynamically adjusted, such as based on physiological parameter data of the patient.

FIG. 1 is an example dual sequential defibrillation system 100 that includes a timing device 110 and two defibrillators 150a, 150b, or defibrillation capable devices. The timing device 110 provides notification outputs to assist a user with timing an administration of electrotherapy from each of the defibrillators 150a, 150b. A user can sequentially actuate the shock buttons 152a, 152b of the defibrillators 150a, 150b, using the output(s) of the timing device 110 to assist with a timing interval separating the sequential electrotherapy administrations.

The timing device 110 includes a timing interval module 120, an output module 130 and a start button 140. A user can press the start button 140 to cause the output module 130 to output two or more notifications that are spaced apart by a time interval 121. The user can use the two or more notifications to assist with actuating the shock buttons 152a, 152b of the defibrillators 150a, 150b to administer sequential electrotherapies. The start button 140 can be any suitable input that can trigger and/or instruct the output module to output the notifications to the defibrillators. The start button 140 can be a physical button actuated by a user or could be any other input from the user, such as a voice prompt or the like.

The timing interval module 120 includes the time interval 121, a timer 122 and an optional adjustment 123. The time interval is the elapsed time between the first notification by the output module 130 and a second notification. That is, the time interval 121 is an inter-shock time interval to space the sequential administration of electrotherapies. The time interval 121 can be a predetermined, or preprogrammed, value that can be based on clinical evidence, clinical procedure, best practices, or other pertinent data. In an example, the time interval 121 can be a predetermined value of 100 milliseconds. Using the 100 ms time interval 121, the timing device 110 outputs a first notification and a second notification 100 ms after the first. A user can use/respond to these first and second notifications, spaced apart by the timing interval 121 of 100 ms, to assist with the administration of electrotherapies from the first and second defibrillators 150a, 150b, by manual actuation of the shock buttons 152a, 152b by the user.

The timer 122 can time the time interval 121 and/or other time values. For example, when the timing device 110 is activated, the timer 122 can countdown the time interval 121 from the first notification and upon expiry can trigger the second notification. In this manner, the time interval 121 is a time value which the timer 122 can apply and/or countdown to trigger the second notification after an elapsed time, the time interval 121, from the trigger of the first notification.

In addition to timing the time interval 121, the timer can time a spacing interval that is a duration of time before the commencement of the timing interval and/or a duration of time between two instances of the timing interval. The spacing interval can be implemented to provide time for a user to prepare for the time interval. For example, user actuation of the start button 140 can initiate the timer 122 to time the spacing interval first, the spacing interval having a duration of 2-5 seconds, and upon the completion of the spacing interval the first notification can be output by the timing device 110. The timer 122 can then time the time interval 121, upon completion of which the second notification is output by the timing device 110. In a further example, upon completion of the time interval 121, the timer 122 can then time the spacing interval again before initiating the time interval 121 and outputs again. In this manner, after activating the timing device 110 a user can have repeated instances of the time interval 121 to assist with the administration of sequential defibrillations by defibrillators 150a, 150b, each instance of the time interval 121, and accompanying outputs, being spaced apart by the spacing interval.

The optional adjustment 123 can be used to adjust one or more of the time interval 121 and the spacing interval. A user can use the adjustment 123 to alter the duration of the time interval 121 and/or the spacing interval. A physical input can be provided on the timing device 110 to allow the user to manipulate the adjustment 123. For example a user actuatable physical input, such as a button and/or knob, can be included on the timing device 110, the user can manipulate/actuate the physical input to adjust the duration of the time interval 121 and/or spacing interval. In a further example, the adjustment 123 can be via a wired or wireless connection that can allow a user to use an external device and/or system to access and use the adjustment 123 of the timing device 110. Alternatively, a remote user, device and/or system can access the adjustment 123 via the wired or wireless connection to the timing device 110 to alter/manipulate the adjustment 123. The ability to adjust the time interval 121 and/or spacing interval via the adjustment 123 can allow the timing interval 121, the inter-shock timing, to be adjusted based on one or more parameters, such as clinical data, experimental data, policy and/or other sources of data/information. Alternatively, the time interval 121 and/or the spacing interval can be a fixed duration that is not adjustable.

The output module 130 can include a visual 132 output, an audible 134 output and/or a tactile output 136. The visual 132 output can include lights 133 and the audible 134 output can include a speaker. The output module 130 provides one or more output formats, such as the visual 132 and/or audible 134, that a user can use to assist with timing the administration of sequential defibrillations by the defibrillators 150a, 150b. A user can actuate the shock button 152a of the first defibrillator 150a in response to a first output by the output module 130 and the user can then subsequently actuate the shock button 152b of the second defibrillator 150b in response to a second output by the output module 130 to administer the sequential defibrillations spaced apart by the inter-shock timing, the time interval 121. The tactile output 136 can include tactile notifications, such as vibrations to provide the first and/or second notifications to the user. The output module 130 can also output the first and/or second notifications in one or more outputs, such as visual 132, audible 134 and/or tactile 136.

The visual 132, audible 134 and/or tactile 136 output of the output module 130 can also provide indications of the spacing interval. For example, the output module 130 can provide a countdown of the spacing interval to the start of the time interval 121 to allow a user to prepare for the time interval 121.

The start button 140 can be an actuatable input of the timing device 110. The user can actuate the start button 140 to initiate timing of the time interval 121 and output of the first and second notifications. In another embodiment, actuation of the start button 140 can initiate the spacing interval followed by the time interval 121 and output of the first and second notifications. The timing of the spacing interval, time interval 121 and output of the first and second notifications can continue until stopped by the user, such as by further actuation of the start button 140. Alternatively, or additionally, the start button 140 can include an audible input, allowing a user to initiate the timing device 110 by verbally stating a command, or sound, to the timing device 110.

The timing device 110 can also be a training device or tool to train a user to administer sequential defibrillations based on the time interval 121. A user can use the timing device 110 to develop a sense of the time interval 121 to allow the user to reproduce the time interval 121 at a later time, such as the administration of sequential defibrillations. The user can practice with the timing device 110, responding to the notifications spaced apart by the time interval 121. When the user is in a DSD situation, the user is able to substantially reproduce the time interval 121 to administer the sequential defibrillations.

Alternatively, the timing device 110 can be a software implementation on an existing device, such as a computing device or medical device. The user can interact with the device to recall the timing device 110 program to assist with providing notifications related to the timing of the administration of sequential defibrillations. For example, the timing device 110 can be an application on a cell phone, tablet and/or computer that the user can launch to receive the notifications, or cues, based on the time interval 121. The timing device 110 application can use the hardware of the device to provide the visual 132, audible 134 and/or tactile notifications to the user.

The timing device 110, features/functionality and/or portions thereof can also be integrated in one of the defibrillators 150a, 150b. For example, the time interval module 120 and the output module 130 can be integrated in one or both of the defibrillators 150a, 150b. In a DSD situation, the user can select to operate one of the defibrillators 150a, 150b, in a timed defibrillation mode. The defibrillator 150a, 150b operating in the timed defibrillation mode can delay administering a shock for a duration equivalent to the time interval 121. To administer the DSD therapy/treatment, the user can simultaneously actuate the shock buttons 152a, 152b of the defibrillators 150a, 150b. In the defibrillator operating in the timed defibrillation mode, the actuation of the shock button is similar to pressing the start button 140 of the timing device 110. In the timed defibrillation mode, the time interval module 120 times the time interval 121 and upon expiry of the time interval 121, the output module 130, instead of providing a notification, causes the administration of the defibrillation, shock, and/or electrotherapy from the defibrillator operating in the timed defibrillation mode.

The timing device 110 can also account for variations between defibrillation capable devices. Defibrillation capable devices, such as defibrillators 150a and 150b, can have a delay between the actuation/triggering of a shock and the delivery of the shock. The timing device 110 can include a library of defibrillation capable devices and associated triggering-delivery delays for each. A user can select the particular defibrillation device(s) being used, such as defibrillators 150a and 150b, and the timing device 110 can modify the time interval 121 to account for the triggering-delivery delay inherent in each of the defibrillation capable devices. In this manner, the notifications of the timing device 110 are spaced apart by the modified time interval 121 such that the shock delivery from each of the defibrillators 150a, 150b, is delivered spaced apart by the desired time interval selected and/or input by the user initially.

FIG. 2 is an example method 200 of timing a dual sequential defibrillation. At 202, an optional adjustment and/or manual setting of the time interval can be done. If no adjustment or setting is performed, a default time interval can be used as the inter-shock timing interval. At 204 a timer can be initiated. The timer can time one or both of a time interval and a spacing, or long, interval that can delay the start of the time interval and/or provide a duration between two or more time intervals. At 206, optionally a pause for a long interval can occur. The long interval can provide a preparation period prior to the time interval. At 208 the first notification can be provided, which can begin the start of the time interval duration. The first notification can cause, or signal to cause, a first defibrillation to be administered. At 210, a pause for the time interval occurs at the conclusion of which a second notification is provided at 212. The second notification can cause, or signal to cause, a second defibrillation to be administered. Optionally, the time interval, and optional long interval, cycle can repeat 214. At 216, the timer can be optionally stopped, such as a by an input or as predetermined/preprogrammed.

Figure 3:
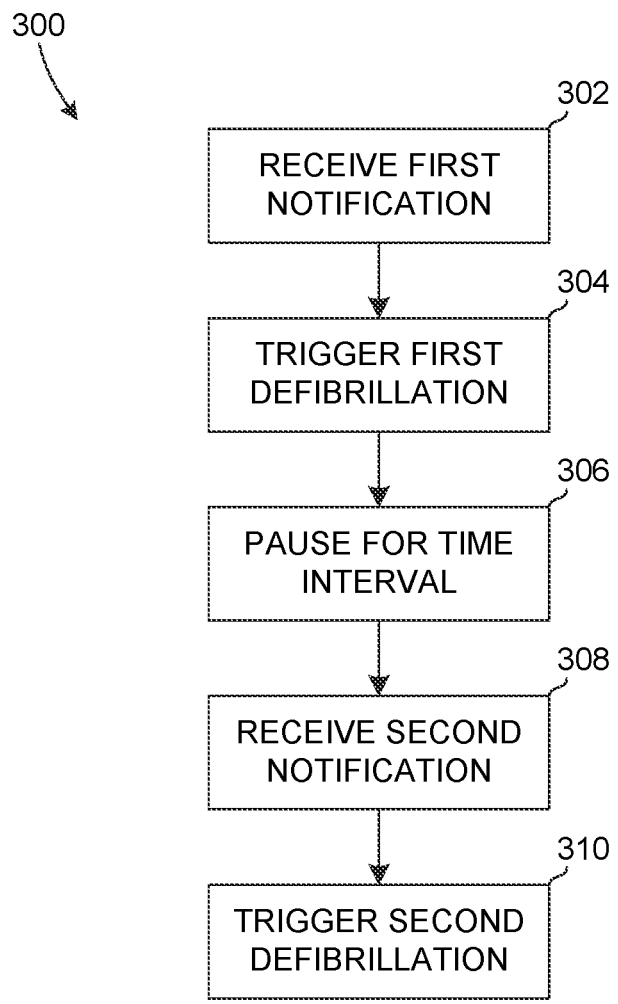
FIG. 3 illustrates an example method of administering a dual sequential defibrillation.

FIG. 3 is an example method 300 of administering a dual sequential defibrillation. At 302 a first notification is received to cause a first defibrillation to be triggered at 304. At 306, a pause for the time interval is awaited until the second notification is received at 308 to cause the second defibrillation to be triggered at 310. The method 300 allows for the administration of sequential defibrillations that are spaced the time interval apart from each other. Reception of the first and second notifications 302, 308 can cause the triggering of the first and second defibrillations 304, 310, either directly or indirectly.

Figure 4:
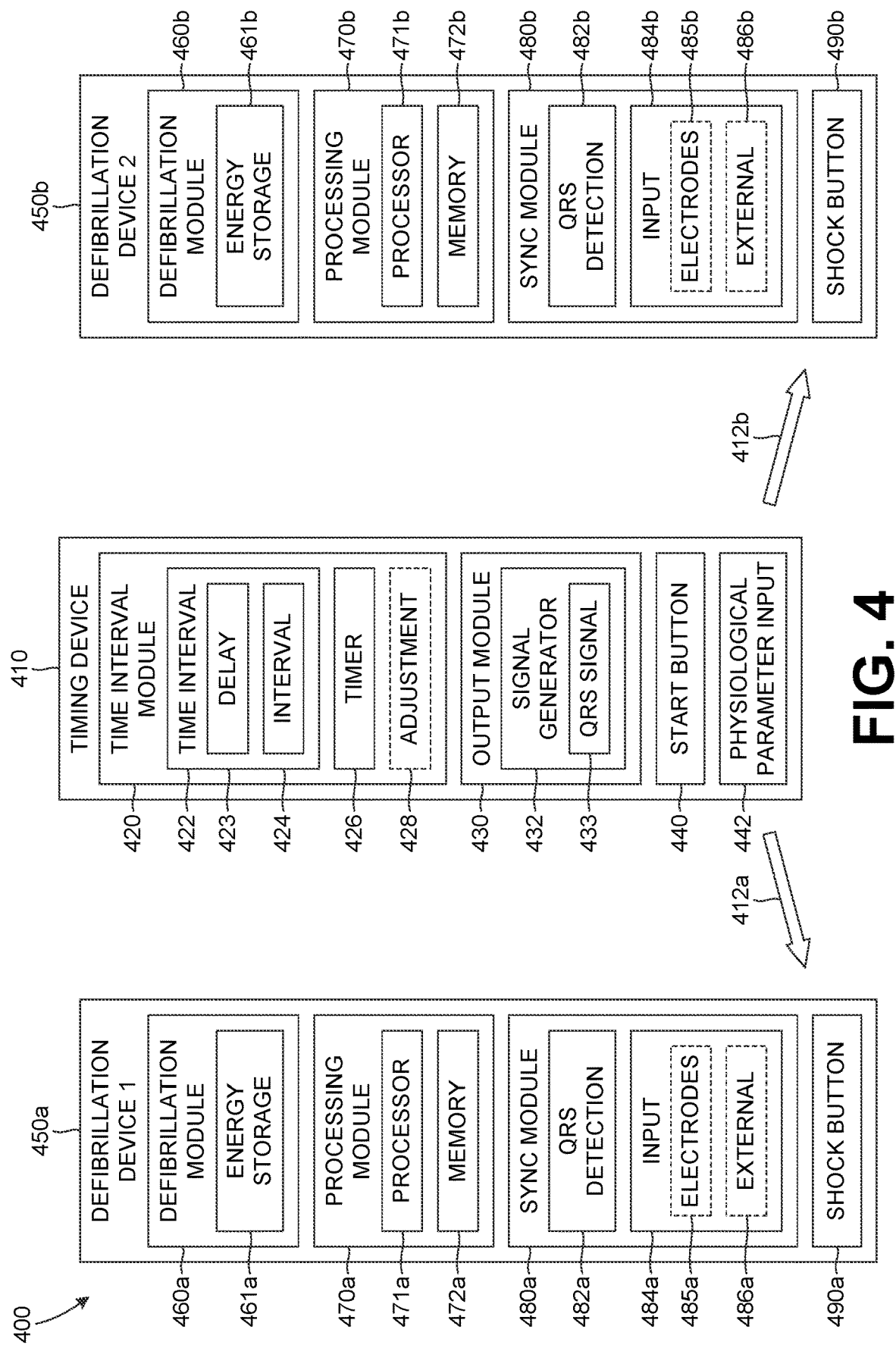
FIG. 4 illustrates a further example dual sequential defibrillation system.

FIG. 4 is an example dual sequential defibrillation system 400 that includes a timing device 410 in communication with two defibrillation devices 450a, 450b. Each of the defibrillation devices 450a, 450b include a sync module 480a, 480b that can administer an electrotherapy, such as a defibrillation or shock, by the defibrillation device 450a, 450b based on a detected electrocardiogram (ECG) feature, such as a QRS complex. The timing device 410 can communicate a signal, mimicking the detectable ECG feature, to each of the defibrillation devices 450a, 450b to cause each of the defibrillation devices 450a, 450b to administer an electrotherapy. In a DSD treatment, the timing device 110 can space apart the signals to each of the defibrillators 450a, 450b by an interval 424 to cause the electrotherapy from the defibrillation devices 450a, 450b to be administered, or output, in a sequential manner.

The defibrillation devices 450a, 450b can include a defibrillation module 460a, 460b, a processing module 470a, 470b, the sync module 480a, 480b and a shock button 490a, 490b. The defibrillation modules 460a, 460b can include an energy storage 461a, 461b, such as a capacitor, that can store and release electrical energy based on the electrotherapy, or defibrillation, being administered. The processing modules 470a, 470b, can include a processor 471a, 471b and memory 472a, 472b. The processors 471a, 471b can control one or more features and/or functions of the defibrillation devices 450a, 450b, including the processing and/or analysis of data received by the defibrillation devices 450a, 450b, such as physiological parameters of a patient coupled to the defibrillation devices 450a, 450b. The memory 472a, 472b can store instructions for execution by the processors 471a, 471b and/or can store collected data, including received patient physiological parameters and/or data regarding one or more treatments/electrotherapies administered by the defibrillation device 450a, 450b. Data stored in the memory 472a, 472b can be exported from the defibrillation device 450a, 450b, such as after a treatment or use of the defibrillation devices 472a, 472b, for review.

The sync modules 480a, 480b can include QRS detection 482a, 482b and input 484a, 484b, which can receive physiological data, such as an ECG signal. The defibrillation devices 450a, 450b can be operated in a sync mode to time the delivery of an electrotherapy/defibrillation by the defibrillation device 450a, 450b. The sync modules 480a, 480b can receive physiological data to provide such timing. ECG, or other physiological, data can be received by the sync modules 480a, 480b from an input 484a, 484b of the defibrillation devices 450a, 450b. The input 484a, 484b can be connected to electrodes 485a, 485b to receive the ECG data, or the ECG data can be provided by an external device or system that can provide ECG data via an external input 486a, 486b, to the defibrillation devices 450a, 450b. In the example system 400 the timing device can be connected to the defibrillation devices 450a, 450b by the inputs 484a, 484b.

The sync modules 480a, 480b receive the ECG data and the QRS detection 482a, 482b analyzes the ECG data to determine features indicative of a QRS complex therein. Operating in sync mode, the defibrillation device 450a, 450b is prompted to administer a defibrillation by actuation of the shock button 490a, 490b. In response, the sync module 480a, 480b analyzes the received ECG and time delivery of the defibrillation from the defibrillation device 450a, 450b to occur during or at a specified interval following a QRS complex. Administration of the defibrillation during or at a specified interval following the QRS complex avoids/prevents administration of the defibrillation during another part of the cardiac cycle, such as during a T-wave as this can be proarrhythmic.

The timing device 410 can include a time interval module 420, an output module 430 and a start button 440. In response to an actuation of the start button 440, or other triggering input, the timing device 410 can initiate a timer 426 and output a first signal 412a, via the output module 430, to the first defibrillation device 450a to cause the first defibrillation device 450a to output an electrotherapy, such as a defibrillation to a patient. The timer 426 runs for the duration of an interval 424 and upon expiry of the timer, the timing device 410 outputs a second signal 412b, via the output module 430, to the second defibrillation device 450b to cause the second defibrillation device 450b to output an electrotherapy, such as a defibrillation to the patient. In this manner, the timing device 410 causes the sequential administration of electrotherapies from the defibrillation devices 450a, 450b, the electrotherapies being temporally spaced apart by the interval 424, the inter-shock time interval. In an embodiment, the inter-shock time interval 424 can be a pre-determined and/or preset duration, such as 100 ms. The interval 424 can be optionally adjusted by a user, device and/or system and/or can be updated, or modified, based on clinical data, such as research studies, that provide further guidance regarding a preferred interval 424.

Additionally, preset and/or predetermined limits to the interval 424 can be included in the timing device 410 to prevent a user, device and/or system, such as an upper limit preventing the interval from being set to a value of greater than 1 second. Similarly, a preset/predetermined lower limit, such as 50 ms, can also be included. The predetermined limits, upper and/or lower, can be based on the clinical data and/or such that the inter-shock timing interval is maintained within an acceptable range based on efficacy of the dual shock therapy being administered. Additional predetermined limits, such as a range(s) of inter-shock timing intervals can also be included. The predetermined range can prevent a user from inputting or selecting an inter-shock timing interval that falls within the restricted predetermined range. The predetermined range can be located between the upper and lower predetermined limits, creating two, interspersed ranges of acceptable inter-shock timing intervals. Restriction of a range of potential inter-shock timing intervals can be based on clinical research, the efficacy of one or more dual defibrillation treatments using inter-shock timing intervals within the restricted range and/or based on other data/inputs. The predetermined limits can be optionally revised and/or altered, such as by a user, device and/or system, if required and/or desired. Revision and/or alteration of the predetermined limits can require authentication and/or verification of a user and/or their credentials to allow such revisions and/or alterations to be made by a user.

Similarly, user authentication and/or verification can allow inter-shock timing outside of the predetermined limits during a treatment session. For example, a user, device and/or system can decide/suggest an inter-shock timing interval that is not contained within the predetermined limits of the timing device 410. A user can provide authentication and/or credential information to the timing device 410, such as by a user code and/or a user carried authentication device/element, to allow the user to operate the timing device outside of the predetermined limits.

The time interval module 420 can include a library of defibrillation capable device and associated triggering-delivery delays, the delay between triggering and delivery of a shock by the defibrillation capable device. The library can be optionally updated to include additional defibrillation capable devices and/or updated triggering-delivery delays. Alternatively, or additionally, the timing device 410 can query or receive triggering-delivery delay information for a defibrillation capable device from a user, device and/or system. The time interval module 420 can alter the interval 424 based on the triggering-delivery delay information so that the actual administration of the defibrillations by the defibrillation devices 450a, 450b are spaced apart by the pre-determined and/or input interval 424. For example, the pre-determined interval 424 can be 100 ms and a triggering-delivery delay of the defibrillation device 450a can be 10 ms and for the defibrillation device 450b the delay can be 20 ms. To account for the triggering-delivery delays, the time interval module 420 can modify the pre-determined interval 424 to 90 ms. The 100 ms interval 424 is first shifted an additional 10 ms to account for the triggering-delivery delay of the defibrillation device 450a and then shortened by 20 ms to account for the triggering-delivery delay of the defibrillation device 450b, such that the interval between the actual administration of the shocks from the defibrillation devices 450a, 450b are spaced apart by the pre-determined, or input, interval 424 of 100 ms.

The time interval module 420 can include a time interval 422, the timer 425 and an optional adjustment 428. The time interval 422 can include a delay 423 and the interval 424. The interval 424 is the spacing, or time duration, between administration of the first and second signals 412a, 412b by the timing device 410. The delay 423 is a duration that can space apart occurrences of the interval 424, such as during a repeating cycle of intervals 424, and/or can be an initial delay, or duration of time, prior to the initiation of the interval 424. For example, upon starting the timing device 410, the delay 423 can be waited prior to beginning the interval 424, at the beginning of which the first signal 412a is output by the timing device 410 and at the expiry of which the second signal 412b is output by the timing device 410. The timer 426 can time both the delay 423 and/or interval 424 of the time interval 422. The optional adjustment 428 can be a physical or electrical input by a user, device and/or system to adjust the time interval 422. The adjustment 428 can adjust one or both the delay 423 and the interval 424 of the time interval 422. Alternatively, one or both of the delay 423 and interval 424 can be fixed values that cannot be adjusted.

The output module 430 can include a signal generator 432 to generate the signals 412a and 412b. The generated signals 412a, 412b can be a QRS signal 433. That is, the signal generator can generate a signal that mimics the signal characteristics/morphology of a QRS signal. While operating in a sync mode, the defibrillation devices 450a, 450b can receive the QRS-like signals 412a, 412b from the timing device 410 to trigger administration of electrotherapies therefrom. The output module 430 can output the first signal 412a based on an initiation of the interval 424 and can output the second signal 412b at the expiry of the interval 424.

To receive the signals 412a, 412b, the timing device 410 can be coupled to the external inputs 486a, 486b or to the electrodes input 485a, 485b to provide the QRS-like signal to the defibrillation devices 450a, 450b. The coupling between the timing device 410 and the defibrillation device 450a, 450b can be through a wired or a wireless connection via which the signals 412a, 412b can be transmitted.

To start the timing device, a user can actuate the start button 440, which can be a physical button actuatable by a user. Additionally, or alternatively, the start button can be an input, rather than a physical button, to cause the timing device 410 to start. As an input, the start button 440 can receive a signal from an external device or system to start the device 410. The input can also include other input forms, such as an audible input. As an audible input, the user can provide a verbal command or cue to the timing device 410 to start the device 410.

In an example, the timing device 410 can be coupled to the defibrillation devices 450a, 450b and a user, device and/or system can start the timing device 410. The timing device 410 can await a delay, such as 2-5 seconds, during which a user can depress the shock buttons 490a, 490b of each of the defibrillation devices 450a, 450b which are operating in a sync mode. Since the defibrillation devices 450a, 450b are operating in a sync mode, the actuation of the shock buttons 490a, 490b does not cause the immediate delivery of a defibrillation, instead each defibrillation device 450a, 450b awaits detection, by the sync modules 480a, 480b, of a QRS complex to administer the defibrillations. After the delay 423, the timing device 410 initiates the interval 424 and outputs the first, QRS-like, signal 412a to cause the first defibrillation device 450a to output a first defibrillation. The timer 426 times the interval 424 and upon completion of the duration specified by the interval 424, the timing device 410 outputs the second, QRS-like, signal 412b to cause the second defibrillation device 450b to output a second defibrillation. The first and second defibrillations are administered sequentially and are separated by the interval 424, the inter-shock timing interval. Alternatively, the defibrillations can be administered simultaneously, with substantially no separation between the administered shock, or the defibrillations can be administered such that a later administered shock at least partially overlaps with a previously administered shock. The interval 424 can be suitably adjusted to cause the administration of simultaneous or overlapping defibrillations.

The timing device 410 can output multiple series of the time interval 422 if needed to cause the sync modules 480a, 480b of the defibrillation device 450a, 450b to administer the sequential defibrillations spaced apart by the interval 424. In an embodiment, the sync modules 480a, 480b can require more than one QRS signal to be detected before administration of the defibrillation timed with a detected QRS signal. In such an embodiment, the timing device 410 can supply multiple instances of the signals 412a, 412b spaced apart by the interval 424.

The timing device 410 can also include a physiological parameter input 442 that can receive physiological parameter data of a patient to which the defibrillation devices 450a, 450b are coupled to. To receive the physiological parameter data, one or more sensors can be connected to the patient and the timing device 410 and/or one or more users, devices, such as defibrillation devices 450a, 450b, and/or systems can provide the physiological parameter data to the timing device 410. The timing device 410 can determine and/or alter the interval 424 based on the received physiological parameter data. Additionally, the received physiological parameter data can allow the timing device 410 to detect the administration of shocks by one or both of the defibrillation devices 450a, 450b. Alternatively, the timing device 410 can be connected to, or in communication with, the defibrillation devices 450a, 450b to detect the administration of shock by the defibrillation devices 450a, 450b. Such detection can include a sensor connected to, or communicating with, the timing device 410, the sensor detecting current flow through electrode leads of the defibrillation devices 450a, 450b. By detecting the administration of the shocks, the timing device 410 can determine an actual time interval between the administrated shocks. This time interval data can be stored and/or communicated to a user, device and/or system, such as for inclusion in a treatment report and/or for modification of subsequent dual sequential shock administrations to the patient. Additionally, the timing device 410 can use this information to determine triggering-delivery delays for the defibrillation capable devices based on the outputs 412a, 412b and any delay in the administration of the shocks from the defibrillation devices 450a, 450b. This triggering-delivery delay information can be stored and/or communicated to a user, device and/or system.

The timing device 410 is shown in FIG. 4 as a separate device of the system 400. In other embodiments, all or a portion of the features and/or functionality of the timing device 410 can be incorporated in one or more defibrillation capable devices, such as defibrillation device 450a and/or 450b.

Figure 5:
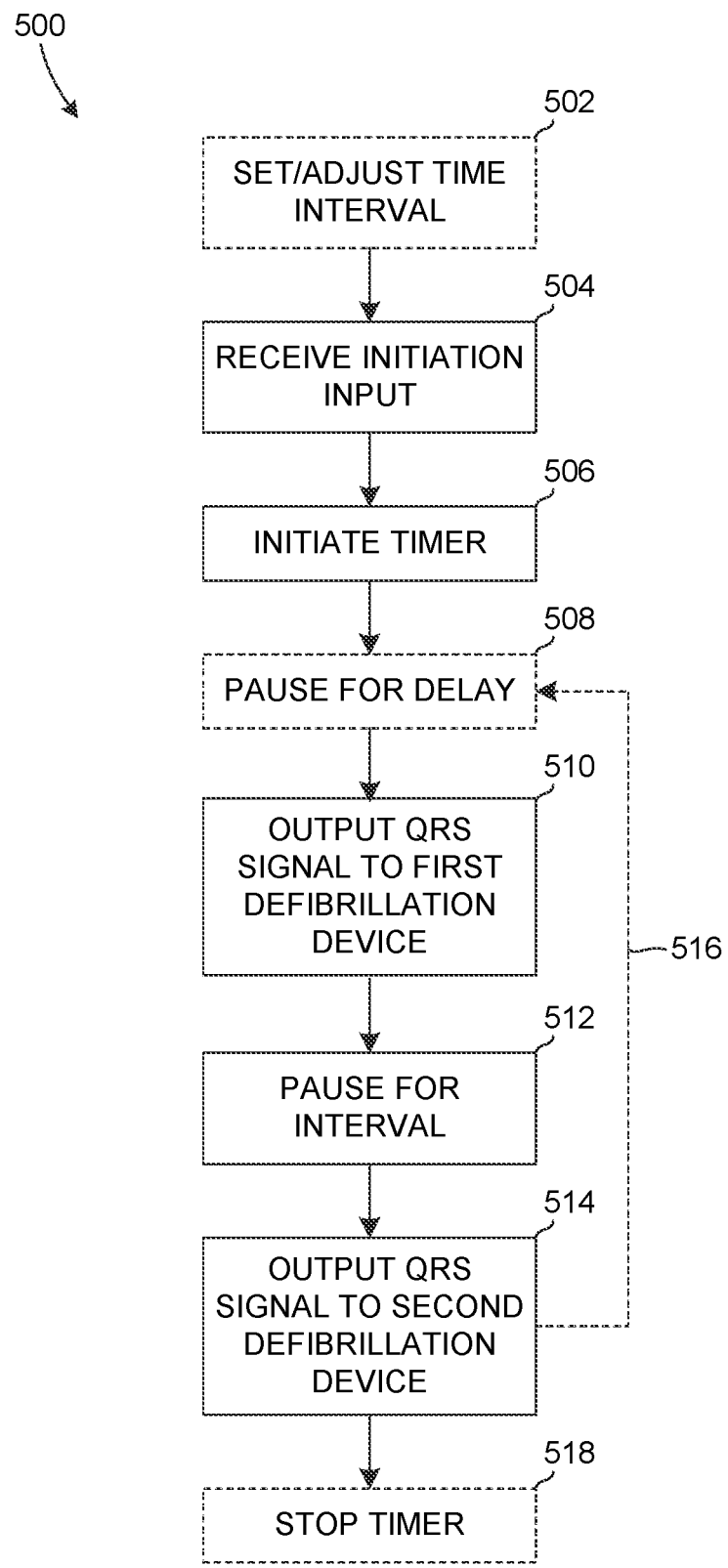
FIG. 5 illustrates a further example method of timing a dual sequential defibrillation.

FIG. 5 is an example method 500 of timing a dual sequential defibrillation using QRS signals. At 502, optionally, the time interval, or inter-shock timing interval, can be set and/or adjusted. Similarly at 502, the delay can also be optionally set/adjusted. At 504, an initiation input can be received to initiate the timer at 406. The input can be a physical actuation of an element, such as a switch, and/or can be an electrical input, such as a received signal. If an optional delay is included, at 508 a pause for the delay can occur. At 510 a QRS signal can be output to a first defibrillation device. The QRS signal can cause the first defibrillation device, operating in a sync mode, to administer a first defibrillation. At 512 a pause for the interval is waited, the interval being the inter-shock timing interval. Upon completion of the duration of the interval, a QRS signal is output to the second defibrillation device at 514. The QRS signal can cause the second defibrillation device, operating in a sync mode, to administer a second defibrillation. Administration of the second defibrillation spaced in any interval from simultaneously to temporally apart from the administration of the first defibrillation by the interval 512. At 516, optionally, the process can be repeated if needed, such as if a series of QRS signals are required before causing the defibrillation devices to administer defibrillations. At 518, the timer can be optionally stopped, such as by a user or device/system. Alternatively, the process 500 can be terminated by the output of the QRS signal to the second defibrillation device at 514 and/or by detection of the administration of one or more of the defibrillation shocks. Detection of the administration of one or more of the defibrillation shocks can be made by a timing device performing the process 500 and/or by another device and/or system, capable of detecting the defibrillation administration(s), in communication with a device, system and/or user performing the process 500.

Figure 6:
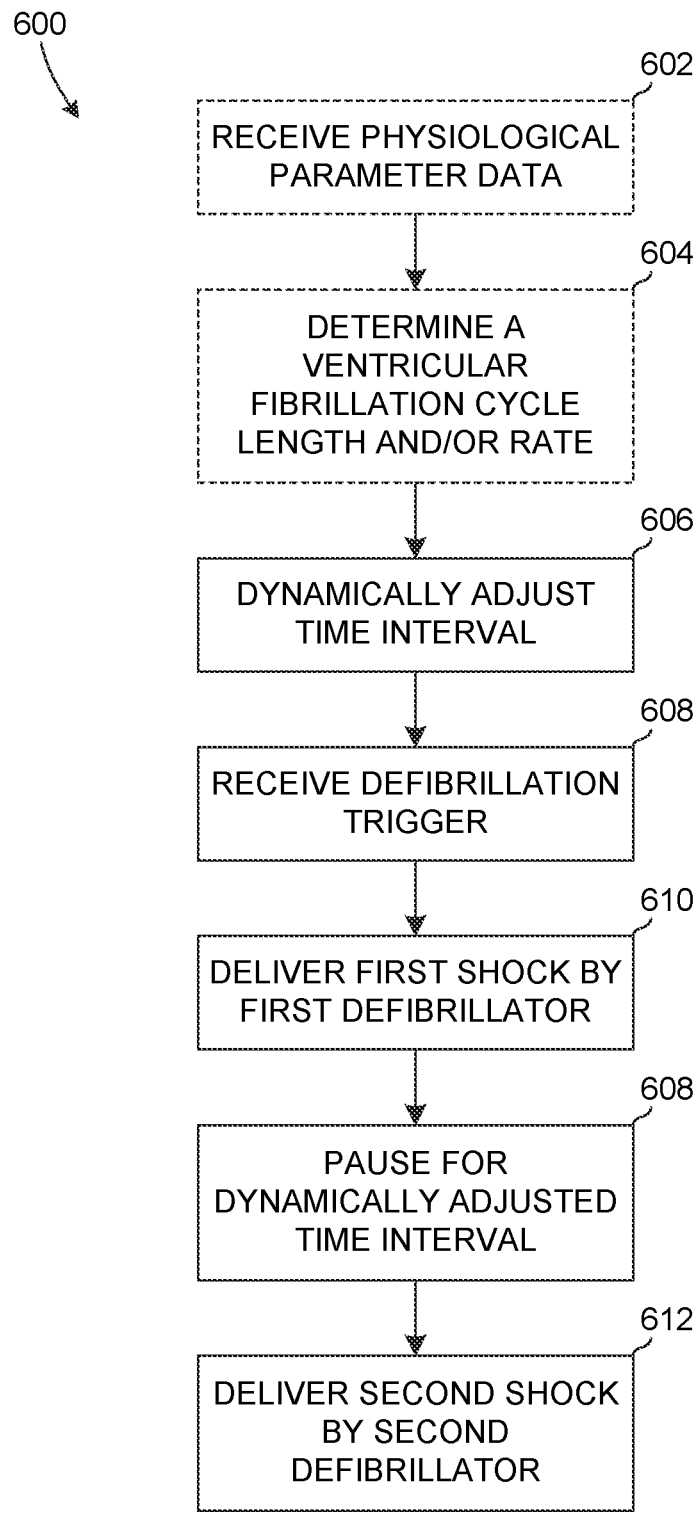
FIG. 6 illustrates an example method of dynamically adjusting a timing interval of dual sequential defibrillation administration.

FIG. 6 is an example method 600 of dynamically adjusting a timing interval of dual sequential defibrillation (DSD) administration using two defibrillation devices and a timing device. The timing interval, or inter-shock timing interval, can be dynamically adjusted, such as based on physiological data. The physiological data can include a ventricular fibrillation (VF) cycle length or VF rate. Based on the physiological data, and/or analysis thereof, the inter-shock timing interval can be adjusted.

In an example, the defibrillation devices can each measure a VF cycle length and communicate with each other to reach a consensus of the rate, such as within a range of +/−1 Hz of each other. The VF cycle length information can then be used by one of the defibrillation devices and/or the timing device to adjust the inter-shock timing interval. The DSD administration can use the adjusted inter-shock timing interval to cause the sequential administration of defibrillations spaced apart by the adjusted inter-shock timing interval.

In another embodiment, the defibrillation device selected to administer the later, or second, shock can measure the VF cycle length and adjust the inter-shock timing interval accordingly. The adjustment to the inter-shock timing interval can be communicated to the timing device or the second defibrillation device can implement the adjustment itself when the triggering signal is received from the timing device.

To measure the VF length, the defibrillation device(s) can receive ECG data from electrodes coupled to the patient. Additionally, the ECG information can be received during administration of cardiopulmonary resuscitation (CPR) compressions to the patient. The defibrillation devices can include filtering hardware and/or software to remove/minimize artifacts, caused by the chest compressions, from/in the ECG data.

In a further embodiment, the timing device can receive patient physiological information to dynamically adjust the inter-shock timing interval. For example, the timing device can be coupled to electrodes and/or leads to receive ECG data from the patient. Alternatively, the ECG data of the patient can be received from one or more of the defibrillation devices, or other devices/systems, coupled thereto.

At 602, of the method 600, optionally, physiological parameter data can be received. At 604, a VF cycle length and/or rate can be determined, such as from the received physiological parameter data. At 606, the time interval, or inter-shock time interval, can be dynamically adjusted. A trigger to cause defibrillation, such as sequential defibrillation, can be received at 608. At 610, a first shock by a first defibrillator can be delivered. At 614, a second shock by a second defibrillator can be delivered. The deliveries 610 and 612 can be spaced apart by a pause 612, the dynamically adjusted time interval of 606.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the invention in diverse forms thereof.

The invention claimed is:

1. A timing device, comprising:
    a time interval module configured to:
        determine a time interval between a first shock and a second shock;
        generate a first notification comprising a first instruction for a first defibrillator to administer the first shock; and
        generate a second notification comprising a second instruction for a second defibrillator to administer the second shock; and
    an output module configured to cause the first defibrillator to administer the first shock by outputting the first notification to the first defibrillator at a first time and to cause the second defibrillator to administer the second shock by outputting the second notification to the second defibrillator at a second time, the difference between the first time and the second time being based on the time interval.

2. The timing device of claim 1, further comprising a start button configured to receive a user input and to cause, in response to the user input, the time interval module to determine the time interval.

3. The timing device of claim 1, further comprising an input device configured to receive a voice prompt and to cause the time interval module to determine the time interval based on the voice prompt.

4. The timing device of claim 1, wherein the time interval is 100 milliseconds (ms).

5. The timing device of claim 1, wherein the time interval module further comprises a timer configured to:
    based on an expiration of the time interval after the first time, cause the output module to output the second notification at the second time.

6. The timing device of claim 1, further comprising a start button configured to receive an input, and
    wherein the time interval module is further configured to determine a spacing interval between receiving the input and outputting the first notification.

7. The timing device of claim 6, wherein a duration of the spacing interval is within a range of 2-5 seconds.

8. The timing device of claim 1, wherein the output module is further configured to output a visual or audible indication of the output of the first notification or the output of the second notification.

9. The timing device of claim 1, wherein the output module further comprises a signal generator configured to generate a first signal mimicking a first electrocardiogram (ECG) feature and to generate a second signal mimicking a second ECG feature, the first notification comprising the first signal and the second notification comprising the second signal, and
    wherein the first signal causes the first defibrillator to administer the first shock and the second signal causes the second defibrillator to administer the second shock.

10. The timing device of claim 1, wherein the time interval module is further configured to receive a signal representative of a patient physiological parameter, and to adjust the time interval based on the patient physiological parameter.

11. A system comprising the timing device of claim 1, and further comprising:
    the first defibrillator, the first defibrillator being a first external defibrillator in communication with the timing device; and
    the second defibrillator, the second defibrillator being a second external defibrillator in communication with the timing device.

12. The system timing device of claim 11, wherein the second defibrillator is configured to sense a patient physiological parameter and to provide the patient physiological parameter to the timing device,
    wherein the time interval module is configured to generate the first notification and the second notification based on the patient physiological parameter, and
    wherein the second external defibrillator is configured to administer the second shock based on the patient physiological parameter and the time interval.

13. The system of claim 11, wherein the second external defibrillator is configured to measure a ventricular fibrillation cycle length of a cardiac event and to provide the ventricular fibrillation cycle length to the timing device, and
    wherein the time interval module is further configured to adjust the time interval based at least in part on the measured ventricular fibrillation cycle length.

14. The timing device of claim 1, wherein the time interval module is configured to determine the time interval based on a parameter that comprises clinical data, a user input, or a patient treatment protocol.

15. The timing device of claim 1, wherein the output module is configured to output the first notification over a wireless connection between the timing device and the first defibrillator, and
    wherein the output module is configured to output the second notification over a wireless connection between the timing device and the second defibrillator.

16. A method, comprising:
    receiving, from a first defibrillator device, physiological parameter data of a patient;
    determining, based on the physiological parameter data, a time interval between administration of sequential defibrillation shocks;
    generating a first notification comprising a first instruction for the first defibrillator device to administer a first shock among the sequential defibrillation shocks;

generating a second notification comprising a second instruction for the second defibrillator device to administer a second shock among the sequential defibrillation shocks;

causing the first defibrillator device to administer the first shock by outputting the first notification to the first defibrillator device at a first time; and causing the second defibrillator device to administer the second shock by outputting the second notification to the second defibrillator device at a second time, the difference between the first time and the second time being based on the time interval.

17. The method of claim 16, further comprising:

determining a first triggering delay of the first defibrillator device;

determining a second triggering delay of the second defibrillator device;

determining the first time based on the first triggering delay; and determining the second time based on the second triggering delay, wherein outputting the first notification is in response to determining the first time, wherein the first triggering delay is between the first time and the time at which the first defibrillator administers the first shock, wherein outputting the second notification is in response to determining the second time, and wherein the second triggering delay is between the second time and the time at which the second defibrillator administers the second shock.

18. The method of claim 16, wherein generating the first notification comprises generating a signal mimicking an electrocardiogram (ECG) feature, and causing the first defibrillator device to administer the first shock comprises outputting the signal to an ECG detection circuit of the first defibrillator device.

19. The method of claim 16, wherein outputting the first notification to the first defibrillator device at the first time comprises transmitting the first notification over a first wired or wireless connection, and wherein outputting the second notification to the second defibrillator device at the second time comprises transmitting the second notification over a second wired or wireless connection.

* * * * *